(12) United States Patent
Seva et al.

(10) Patent No.: US 9,410,955 B2
(45) Date of Patent: Aug. 9, 2016

(54) METHOD FOR PREDICTING THE RISK OF DEVELOPING A COLONIC NEOPLASIA

(75) Inventors: Catherine Seva, Toulouse (FR); Catherine Do, Toulouse (FR); Audrey Ferrand, Toulouse (FR); Julien Palasse, Toulouse (FR); Marie-Bernadette Delisle, Toulouse (FR)

(73) Assignees: INSERM (INSTITUT NATIONAL DE LA SANTE ET DE LA RECHERCHE MEDICALE), Paris (FR); UNIVERSITE PAUL SABATIER—TOULOUSE III, Toulouse (FR); CENTRE HOSPITALIER UNIVERSITAIRE de TOULOUSE, Toulouse (FR)

( * ) Notice: Subject to any disclaimer, the term of this patent is extended or adjusted under 35 U.S.C. 154(b) by 0 days.

(21) Appl. No.: 14/123,121

(22) PCT Filed: May 31, 2012

(86) PCT No.: PCT/EP2012/060289
§ 371 (c)(1),
(2), (4) Date: Mar. 13, 2014

(87) PCT Pub. No.: WO2012/164035
PCT Pub. Date: Dec. 6, 2012

(65) Prior Publication Data
US 2014/0186366 A1    Jul. 3, 2014

(30) Foreign Application Priority Data
Jun. 1, 2011    (EP) .................................... 11305671

(51) Int. Cl.
*G01N 33/574* (2006.01)
*C07K 16/26* (2006.01)
*G01N 33/74* (2006.01)

(52) U.S. Cl.
CPC .......... *G01N 33/57419* (2013.01); *C07K 16/26* (2013.01); *G01N 33/74* (2013.01); *G01N 2333/595* (2013.01); *G01N 2800/50* (2013.01)

(58) Field of Classification Search
None
See application file for complete search history.

(56) References Cited
U.S. PATENT DOCUMENTS 5,595,756 A * 1/1997 Bally et al. .................... 424/450
7,854,932 B2 * 12/2010 Singh ................. A61K 38/2207
424/130.1
9,217,032 B2 * 12/2015 Pannequin ........... C07K 5/1016
2007/0248608 A1 * 10/2007 Grimes ....................... 424/142.1
2010/0291193 A1    11/2010 Singh et al.
2015/0071912 A1 *  3/2015 Houhou ................. C07K 16/26
424/133.1

FOREIGN PATENT DOCUMENTS

WO    2007/135542 A2    11/2007

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000, 10:398-400).*
Vajdos et al. (J Mol Biol. Jul. 5, 2002;320(2):415-28 at 416).*
Brown et al. (J Immunol. May 1996;156(9):3285-91 at 3290 and Tables 1 and 2).*
Guido et al (Curr Med Chem. 2008;15(1):37-46).*
Clark et al (J. Med. Chem., 2014, 57 (12), pp. 5023-5038).*
Aagaard et al (Advanced Drug Delivery Reviews 59 (2007) 75-86).*
Warzocha et al (Leukemia and Lymphoma, Val. 24. pp. 267-281).*
McKeague et al (J Nucleic Acids. 2012;2012:748913. Epub Oct. 24, 2012).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
Ciccotosto et al., "Expression, processing, and secretion of gastrin in patients with colorectal carcinoma", Gastroenterology, Oct. 1, 1995, pp. 1142-1153, vol. 109, No. 4.
Huang et al., "Increased incidence of colorectal adenomas in follow-up evaluation of patients with newly diagnosed hyperplastic polyps", Surgical Endoscopy, May 9, 2001, pp. 646-648, vol. 15, No. 7.
Smith et al., "Gastrin and gastrin receptor activation: an early event in the adenoma-carcinoma sequence", Gut, Dec. 1, 2000, pp. 820-824, vol. 47, No. 6.
Ferrand et al., "Gastrin and cancer: A review", Cancer Letters, Jul. 8, 2006, pp. 15-29, vol. 238, No. 1.
Do et al., "A New Biomarker That Predicts Colonic Neoplasia Outcome in Patients with Hyperplastic Colonic Polyps", Cancer Prevention Research, Feb. 24, 2012, pp. 675-684, vol. 5, No. 4.
Anonymous, "Colorectal polyp", Wikipedia, Oct. 10, 2011, pp. 1-6, Web.

* cited by examiner

*Primary Examiner* — Brian J Gangle
*Assistant Examiner* — Andrea McCollum
(74) *Attorney, Agent, or Firm* — Whitham, Curtis & Cook, P.C.

(57) ABSTRACT

The present invention relates to an in vitro method for determining whether a patient having hyperplastic polyps is at risk of developing a colonic neoplasia after resection of said hyperplastic polyps, said method comprising the step of determining the level of progastrin expression in a tissue sample of a hyperplastic polyp obtained from said patient.

4 Claims, 6 Drawing Sheets

A

B

METHOD FOR PREDICTING THE RISK OF DEVELOPING A COLONIC NEOPLASIA

FIELD OF THE INVENTION

Figure 1:
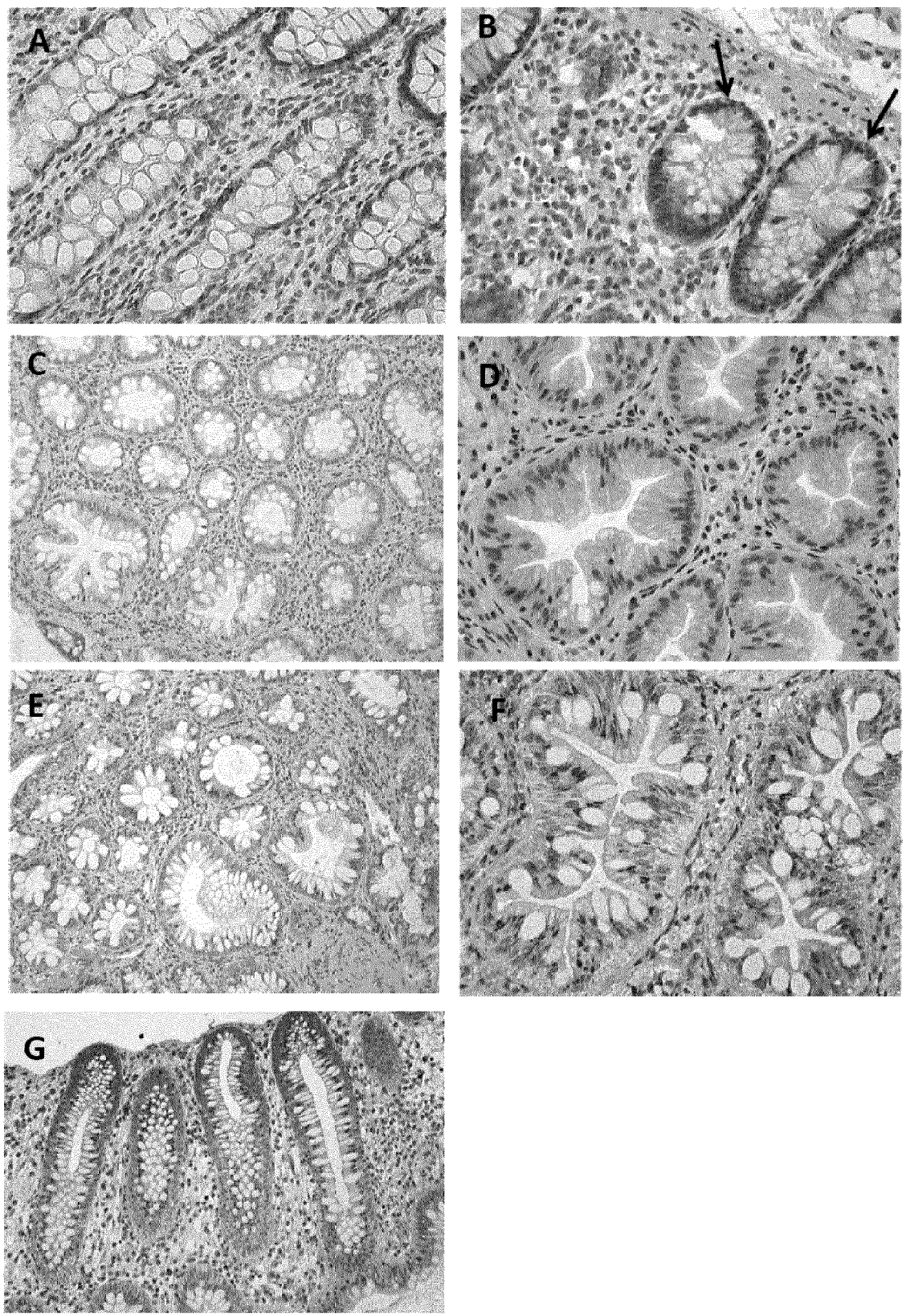

The present invention relates to an in vitro method for determining whether a patient having hyperplastic polyps is at risk of developing a colonic neoplasia after resection of said hyperplastic polyps, said method comprising the step of determining the level of progastrin expression in a tissue sample of a hyperplastic polyp obtained from said patient.

BACKGROUND OF THE INVENTION

Colorectal cancer is a major health problem with over 1.2 million new cases and 608,700 deaths estimated every year in the world. Despite the surgical resection of the primary tumour, around 50% of patients die within five years of diagnosis as a result of local tumour recurrences or distant metastasis. This high mortality is mainly due to a lack of efficient test allowing the detection of patients at an early stage of the disease. Thus, there is an urgent need for new early markers that will help to identify patients with high risk for developing colorectal cancer.

In the general population the most frequently occurring lesion in the colon is the hyperplastic polyp (HP), with prevalence in western populations of 10% to 35%. Hyperplastic polyps (including globlet cell-rich HP, microvesicular HP and mucin poor HP) have long been considered as innocuous lesions with no malignant potential, whereas adenomatous polyps (including tubular, villous, tubulovillous and serrated adenomas) were recognized as neoplastic precursor lesions for colorectal adenocarcinomas.

However, large HP (size>1 cm) and the presence of multiple HP (number>5) in hyperplastic polyposis syndrome have been clearly associated with colorectal adenomas or adenocarcinoma [Renaut A J et al., 2002]. Based on these considerations, in France, clinical practice guidelines from the French National Agency for Accreditation and Evaluation in Healthcare do not recommend colonoscopy for patients with HP, except after resection of one large hyperplastic polyp (≥1 cm) and/or multiple polyps (n≥5) or if there is a family history of hyperplastic polyps. Neither does the American College of gastroenterology [Bond J H 2000 and Rex D K, et al., 2009].

In addition to the cases of large HP and hyperplastic polyposis, more recent studies have suggested a link between HP and sporadic colorectal cancer. Huang, et al. also found that patients with HP on initial colonoscopic examination have an increased incidence of colorectal adenomas on follow-up colonoscopy. However Huang, et al study does not allow to determine which HP is at high risk and do not identify the patients with HP that will develop colonic neoplasia (adenomas/carcinomas) after resection of these initial polyps. Until now, there is no biomarker to predict which HP may have a malignant potential and to identify the subset of patients with HP that will develop colonic neoplasia after resection of these initial polyps and for which a more suitable follow up strategy could be considered (about 40% of the patients according to our study and Huang study). It is also important to identify the 60% of patients with HP that will not develop adenomas or carcinomas after resection of these initial HP because there is no need for these patients to propose a colonoscopy follow up. The current invention identifies and validates such a biomarker.

The hormone precursor progastrin (PG) is recognized as a growth factor which plays an important promoting role in colon carcinogenesis. This hormone precursor is overexpressed in colorectal adenomatous polyps (neoplastic polyps) and carcinomas [Nemeth J. et al., 1993; Siddheshwar R K et al., 2001 and Van Solinge W W et al. 1993. In contrast this prohormone is absent from the healthy colonic tissues. The expression or overexpression of progastrin has never been reported in non neoplastic lesions and in particular in HP neither in human samples nor in animal models. US Patent N° US2010/0291193 discloses the presence of negligible to moderate levels of gastrin mRNA in normal colonic mucosa not significantly different from the mRNA levels observed in a sample of 10 HP. Moreover, no progastrin immunostaining is shown in HP.

SUMMARY OF THE INVENTION

Figure 3:
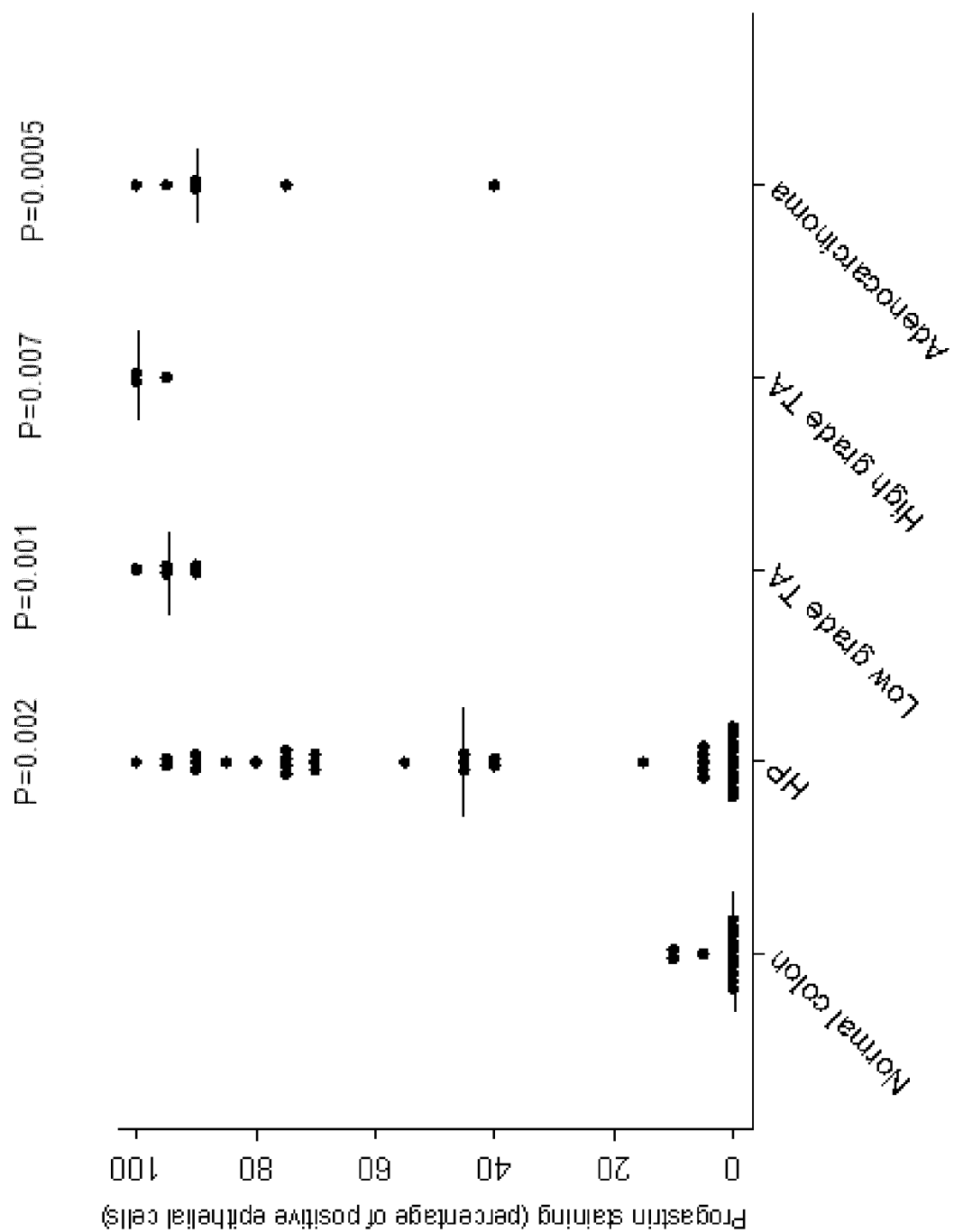

The present invention discloses in a cohort of patients, without history of colorectal pathology (tables 1 and 2), presenting initial HP which are considered as non neoplastic (size≤1 cm and number≤5), that progastrin expression (at the protein level) is significantly higher in HP compared to normal colonic mucosa (p=0.002, FIG. 3). The present invention also discloses that more that 40% of patients displayed a very strong expression of progastrin (progastrin staining in more than 50% of epithelial cells) (table 1 FIG. 1). In addition about 95% of patients with a high staining of progastrin (more than 50% of epithelial cells) have developed adenomas in the 3 to 8 years after resection of the HP whereas none of the patients with no/weak progastrin expression. (progastrin staining <10% of epithelial cells) developed such lesions (FIG. 4B) Thus, in the present invention is provided a method and a prognostic tool (the biomarker, progastrin) for determining which patient having HP will develop colonic neoplasm (adenomas, adenocarcinomas) after resection of said HP.

Thus, the invention relates to an in vitro method for determining whether a patient having hyperplastic polyps is at risk of developing a colonic neoplasia after resection of said hyperplastic polyps, said method comprising the step of determining the level of progastrin expression in a tissue sample of a hyperplastic polyp obtained from said patient.

Moreover, the invention relates to a kit for performing the method according to the invention which comprises means for determining the level of progastrin in a tissue sample of a hyperplastic polyp.

DETAILED DESCRIPTION OF THE INVENTION

Method of Prediction

The invention relates to an in vitro method for determining whether a patient having hyperplastic polyps is at risk of developing a colonic neoplasia comprising the step of determining the level of progastrin expression in a tissue sample of a hyperplastic polyp obtained from said patient.

More particularly, the invention relates to an in vitro method for determining whether a patient having hyperplastic polyps is at risk of developing a colonic neoplasia after resection of said hyperplastic polyps, comprising the step of determining the level of progastrin expression in a tissue sample of a hyperplastic polyp obtained from said patient.

Particularly, the invention relates to an in vitro method for determining which patient having hyperplastic polyps will develop a colonic neoplasia (adenomas, adenocarcinomas) after resection of said hyperplastic polyps, said method comprising the step of determining the level of progastrin expression in a tissue sample of an hyperplastic polyp obtained from said patient.

As used herein, "Progastrin" is the 80 amino acid product formed after cleavage of the twenty-one amino acid signal sequence from preprogastrin (101 amino acids). The amino acid sequence of progastrin is described as the amino acid sequence SEQ ID NO 1.

As used herein, the term "colonic neoplasia" or "colonic neoplasm" denotes a tissue whose cells have lost its normal differentiation with abnormalities of nucleus and/or proliferation present in the large intestine (colon, cecum, rectum) including colorectal adenomas (including tubular, villous, tubulovillous and serrated adenomas) and adenocarcinomas.

As used herein, the term "hyperplastic polyp" denotes a non neoplastic polyp of the large intestine (colon, cecum, rectum) including globlet cell-rich HP, microvesicular HP and mucin poor HP with or without abnormal proliferation [WHO Classification of Tumours of the Digestive System, Fourth Edition and WHO Classification of Tumours, Volume 3 IARC Bosman, F. T., Carneiro, F., Hruban, R. H., Theise, N. D].

According to the invention, the tissue sample of a hyperplastic polyp may be obtained in the distal or proximal colon, as well as in the cecum or rectum.

The tissue samples may be obtained from hyperplastic polyps preserved by methods classically used by anatomopathology department, e.g. paraffin embedded or frozen tissues.

In a preferred embodiment, the method is applied on a patient with hyperplastic polyps for which no endoscopic surveillance is recommended neither in the guidelines from the French National Agency for Accreditation and Evaluation in Healthcare, nor by the American College of Gastroenterology (polyp size lower than 1 cm, less than 5 hyperplastic polyps and no family history of hyperplastic polyps).

Determine the progastrin expression in the tissue sample of a hyperplastic polyp may be performed by determining the expression level of progastrin protein. Any methods that permit to determine the expression of a specific protein in tissues can be used.

Such methods comprise contacting a tissue sample of a hyperplastic polyp sample with a binding partner capable of selectively interacting with progastrin present in the sample. The binding partner may be an antibody polyclonal or monoclonal, an antibody fragment, synthetic antibodies, or other protein-specific agents such as nucleic acid or peptide aptamers. Preferably, the binding partner is a polyclonal or monoclonal antibody.

The preferred method according to the present invention is immunohistochemistry analysis. Antibodies specific for progastrin are preferred for this purpose due to specificity and availability. Several laboratories have generated and characterized specific progastrin antibodies. In addition, such antibodies may be easily generated using techniques well-known to those skilled in the art. The use of antibodies to identify proteins of interest in the cells of a tissue, referred to as immunohistochemistry (IHC), is well established. See for example "Principles and practice of immunoassays" 1991, C. P. Price and D. J. Neoman (eds) Stockton Press, N.Y.

For the detection of the antibody that makes the presence of the protein of interest detectable by microscopy or an automated analysis system, progastrin antibodies may be tagged directly with detectable labels such as enzymes, chromogens or fluorescent probes or indirectly detected with a secondary antibody conjugated with detectable labels. The preferred staining method according to the present invention uses a secondary antibody coupled to an amplification system (to intensify staining signal) and enzymatic molecules. Such coupled secondary antibodies are commercially available, e.g. from Dako, ENVISION® system (a two-step visualization system including an enzyme-conjugated polymer backbone conjugated to a secondary antibody). Counterstaining may be used, e.g. H&E, DAPI, Hoechst.

Other staining methods may be accomplished using any suitable method or system as would be apparent to one of skill in the art, including automated, semi-automated or manual systems.

The method further comprise a step consisting of comparing the expression level of progastrin in the sample with a reference value or threshold value, wherein a difference between said expression level and said reference value is indicative of risk of developing a colonic neoplasia.

In other word, the method further comprise a step consisting of comparing the expression level of progastrin in the sample with a reference value, wherein a difference between said expression level and said reference value is predictive of development of a colonic neoplasia after resection of the HP.

Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtained the optimal sensitivity and specificity according to the function of the test (screening, diagnostic, predictive or prognostic) and the benefice/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the expression levels of progastrin obtained according to the method of the invention with a defined threshold value. In the present invention, by comparing the expression levels of progastrin to the threshold value of 40%, the physician is then able to predict if a patient will develop a colonic neoplasia after resection of this initial polyp.

In a particular embodiment, the method comprises quantification of the expression of progastrin. The expression of the progastrin protein is determined by the percentage of epithelial cells in the whole hyperplastic polyp that express the progastrin protein.

The inventors have established that in colonic tissue of healthy patients who do not suffer from any colonic neoplasia or hyperplastic polyps, less than 10% of the colonic epithelial cells are positive for the expression of progastrin when the measure of progastrin protein is performed by immunohistochemistry (see the results in example 1 and FIG. 3). In the same methodological conditions, they also established that the percentage of colonic epithelial cells positive for the expression of progastrin is significantly higher in HP compared to normal colonic mucosa (median: 45%, p=0.002, FIG. 3).

The inventors clearly established that patients with hyperplastic polyps that present weak progastrin expression, less than 10% of the colonic epithelial cells positive for the expression of progastrin (26% of the patients in the whole cohort table 1) have a 5 years-neoplasm free survival of 100% (FIG. 4B). Patients with hyperplastic polyps that present moderate progastrin expression, 10 to 50% of the colonic epithelial cells positive for the expression of progastrin (34% of the patients in the whole cohort table 1) have a 5 years-neoplasm free survival of 84% (FIG. 4B). This value decreases to 38% for the patients with high progastrin expression (at least 50% of epithelial cells positive for progastrin) (40% of the patients in the whole cohort table 1) In addition, about 95% of patients with hyperplastic polyps that present at least 50% of epithelial cells positive for progastrin have developed adenomas in the 3 to 8 years after resection of the HP whereas none of the patients with weak progastrin expression. (progastrin staining <10% of epithelial cells) developed such lesions (FIG. 4B).

The inventors have established that the association between progastrin staining and neoplasm-free survival is independent from the subject's age, HP localisation and HP size, by performing multivariate analysis (table 2). After adjustment, progastrin expression was still highly significantly associated with adenoma occurrences (p<0.0001). Taken together, these results show that progastrin staining in HP is a strong independent prognostic factor.

Figure 5:
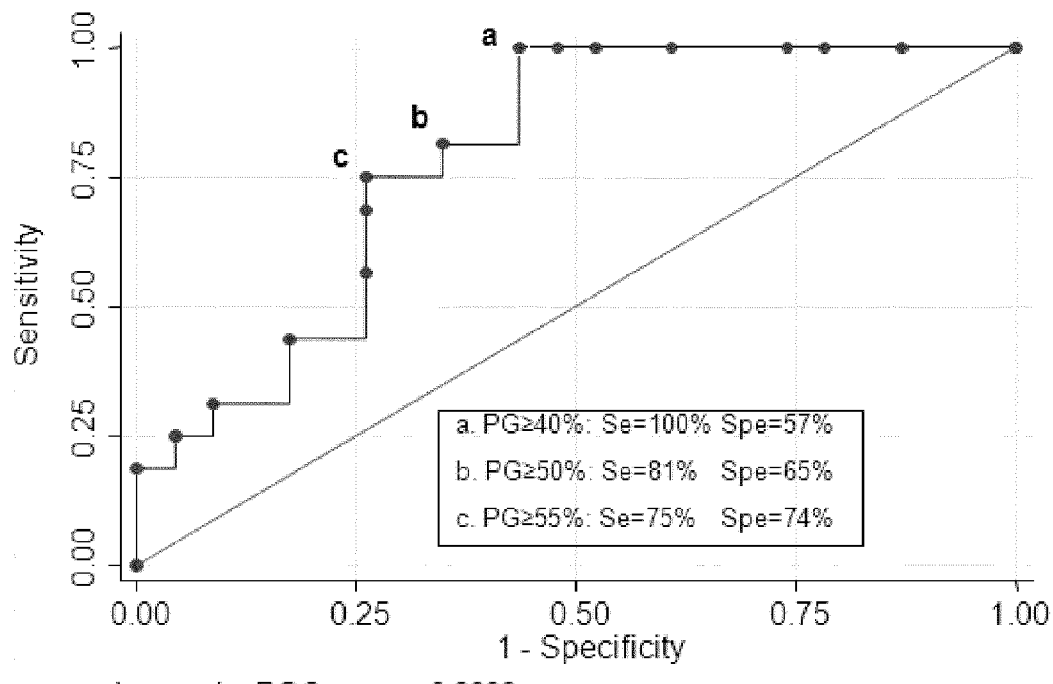
Figure 5:
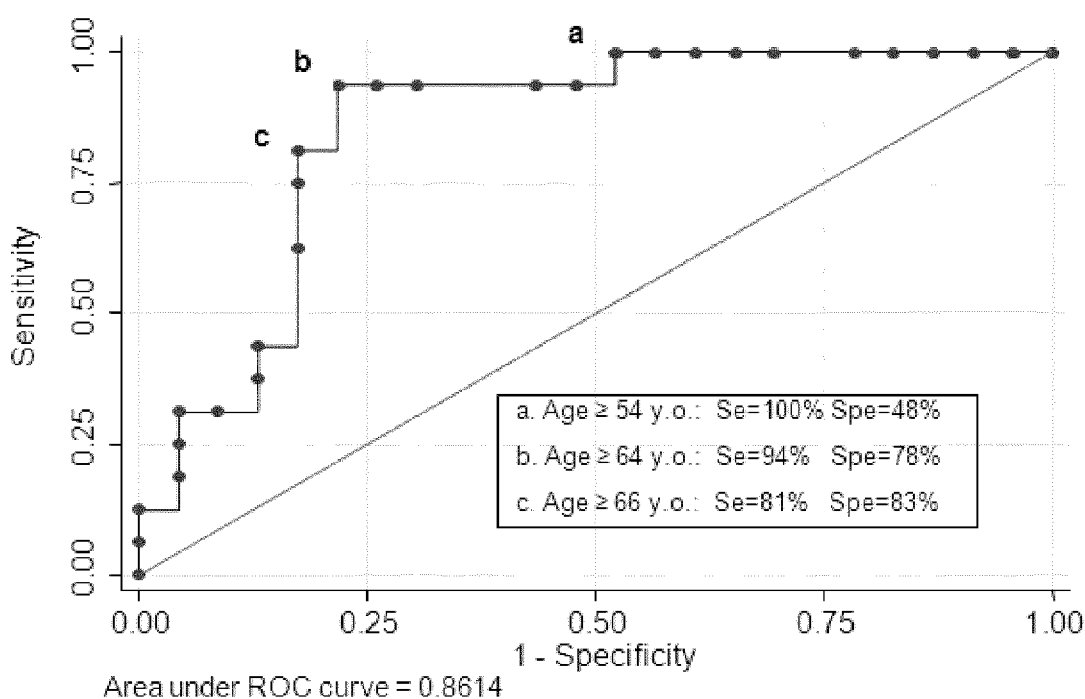

The inventors have established the best "diagnostic" threshold values for expression levels of progastrin to easily predict which patient will further develop a colonic neoplasia after resection of an initial hyperplastic polyp (with a 100% sensitivity to detect all the patients at risk to develop an adenoma and an optimal specificity) (FIG. 5). In other words, there was no false negative patient (NVP=0) in this study.

The present invention also relates to kits for performing the method according to the invention comprising means for determining the level of progastrin expression.

According to the invention, the kits of the invention may comprise an anti-progastrin antibody; and another molecule coupled with a signalling system which binds to said progastrin antibody.

Typically, the antibodies or combination of antibodies are in the form of solutions ready for use. In one embodiment, the kit comprises containers with the solutions ready for use. Any other forms are encompassed by the present invention and the man skilled in the art can routinely adapt the form to the use in immunohistochemistry.

The present invention also relates to progastrin as a biomarker for determining whether a patient having hyperplastic polyps is at risk of developing a colonic neoplasia.

In other word, the present invention relates to progastrin as a biomarker for determining whether a patient having hyperplastic polyps will develop a colonic neoplasia (adenomas, adenocarcinomas) after resection of said polyp.

Therapeutic Method

In another aspect, the invention relates to a method of prophylactic treatment of patient with at risk of developing a colonic neoplasia after resection identified with the method according to the invention by administrating an antagonist of progastrin.

In another embodiment, the invention relates to a method of prophylactic treatment of patient which will develop a colonic neoplasia after resection identified with the method according to the invention by administrating an antagonist of progastrin.

As used herein, the term "method of prophylactic treatment" denotes a treatment which permits to a patient to not have a colonic neoplasia after resection. In other word, the "prophylactic treatment" is a preventive treatment.

In one embodiment, said antagonist of progastrin may be a low molecular weight antagonist, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Preferred small organic molecules range in size up to about 10000 Da, more preferably up to 5000 Da, more preferably up to 2000 Da and most preferably up to about 1000 Da.

In one embodiment, the antagonist may bind to progastrin and block the binding of other compound on progastrin.

In another embodiment, antagonist of progastrin of the invention may be an anti-progastrin antibody which neutralizes progastrin or an anti-progastrin fragment thereof which neutralizes progastrin.

Antibodies directed against progastrin can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against progastrin can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-progastrin single chain antibodies. Progastrin antagonists useful in practicing the present invention also include anti-progastrin antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to progastrin.

Humanized anti-progastrin antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of progastrin are selected.

In a particular embodiment, the antibody anti-progastrin according to the invention may be an antibody as explained in the patent application WO2011045080.

In still another embodiment, progastrin antagonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then, for this invention, neutralizing aptamers of progastrin are selected.

Another object of the invention relates to an antagonist of progastrin for use in the prophylactic treatment of patient with at risk of developing a colonic neoplasia after resection identified with the method according to the invention.

In another embodiment, the invention relates to an antagonist of progastrin for use in the prophylactic treatment of patient which will develop a colonic neoplasia after resection identified with the method according to the invention.

Compounds of the invention may be administered in the form of a pharmaceutical composition, as defined below.

Preferably, said compound is an antagonist of progastrin.

By a "therapeutically effective amount" is meant a sufficient amount of compound to treat and/or to prevent a colonic neoplasia after resection.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific antagonist employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Compounds according to the invention may be used for the preparation of a pharmaceutical composition for the prophylactic treatment of patient with at risk of developing a colonic neoplasia after resection identified with the method according to the invention.

Hence, the present invention also provides a pharmaceutical composition comprising an effective dose of an antagonist of progastrin according to the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

The invention will be further illustrated by the following figures and examples. However, these examples and figures should not be interpreted in any way as limiting the scope of the present invention.

FIGURES

FIG. 1. Progastrin staining in normal colon and hyperplastic polyps (HP).

A: Negative progastrin staining in normalcolon (×40). B: Weak progastrin staining in the bottom of the crypt in normal colon (arrows) (×40). C,D: Progastrin negative HP (respectively, ×20 and ×40). E, F: HP overexpressing progastrin (respectively, ×20 and ×40). G: Positive HP-adjacent normal colon (×20).

Figure 2:
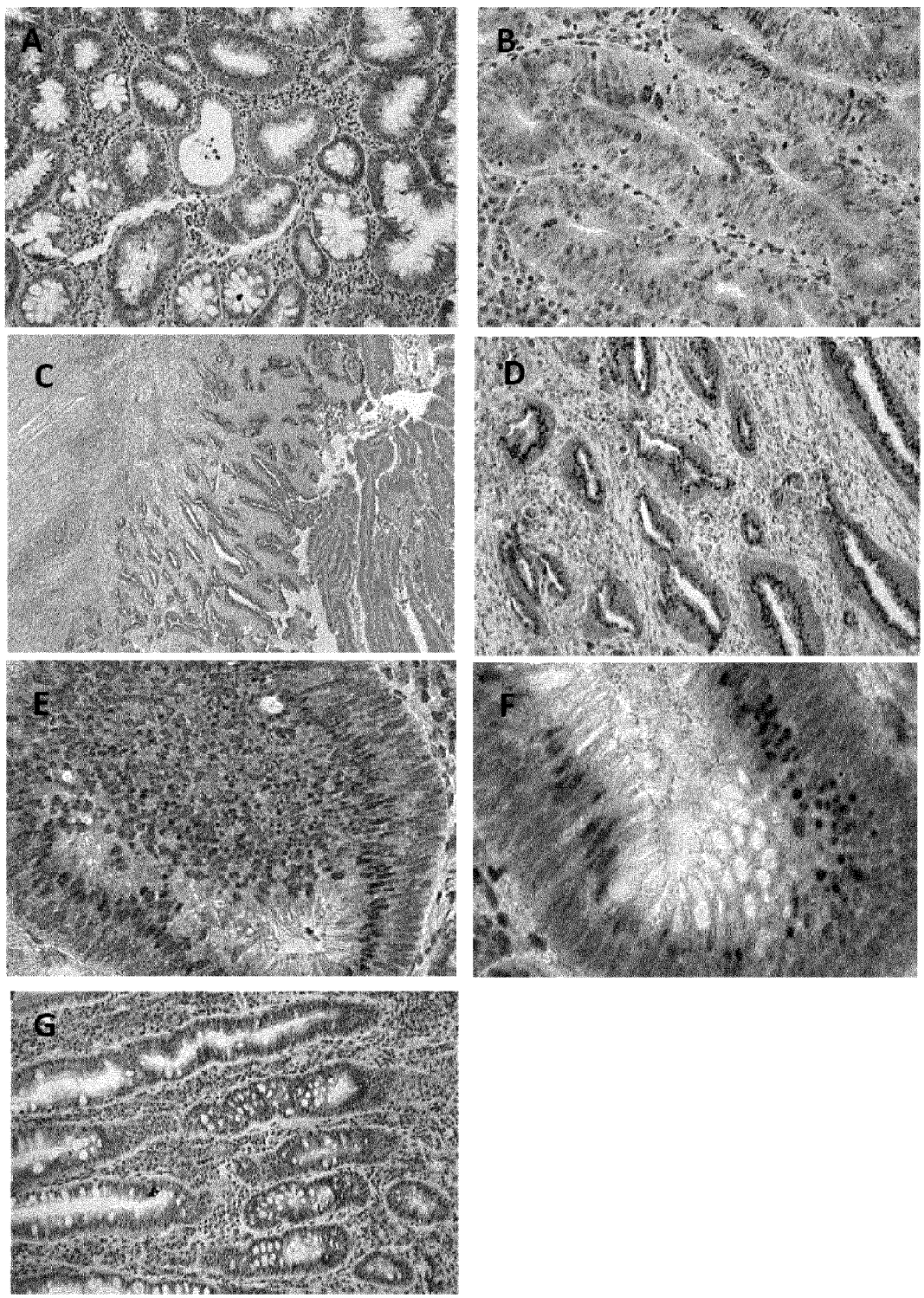

FIG. 2. Progastrin staining in colon adenomas and adenocarcinomas.

A, B: Strong staining in low grade (A, ×20) and high grade dysplasia adenoma (B, ×40). C-F: Strong progastrin staining in adenocarcinomas at different magnificence (×4, ×20, ×40 and ×100). G: adenocarcinoma-adjacent normal tissue positive for progastrin.

FIG. 3. Percentage of progastrin positive cells for normal colon, hyperplastic polyps (HP), low grade dysplasia tubular adenoma (TA), high grade dysplasia TA, and adenocarcinoma. Wilcoxon tests were performed to compare the percentage of progastrin positive cells in the different tissues to the percentage in normal colon.

Figure 4:
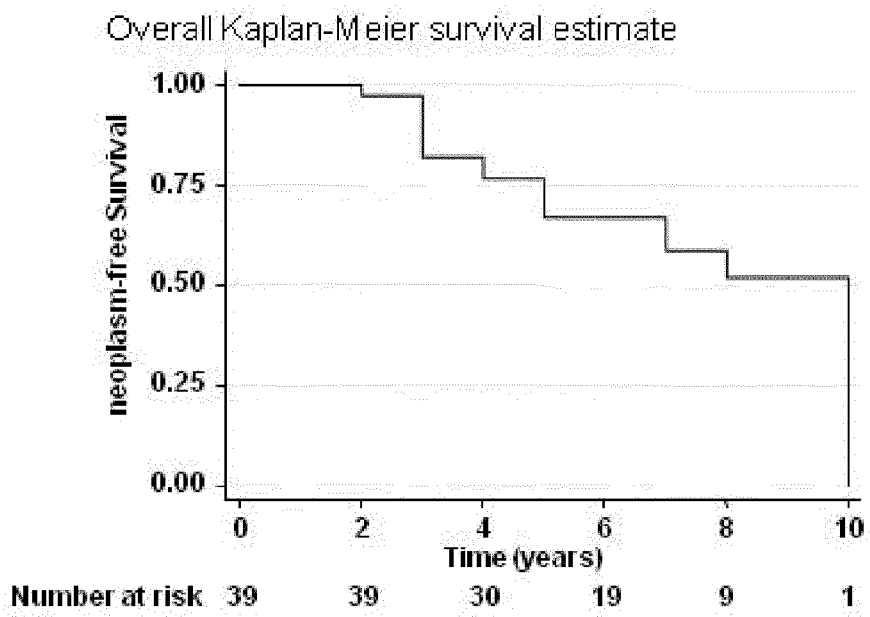
Figure 4:
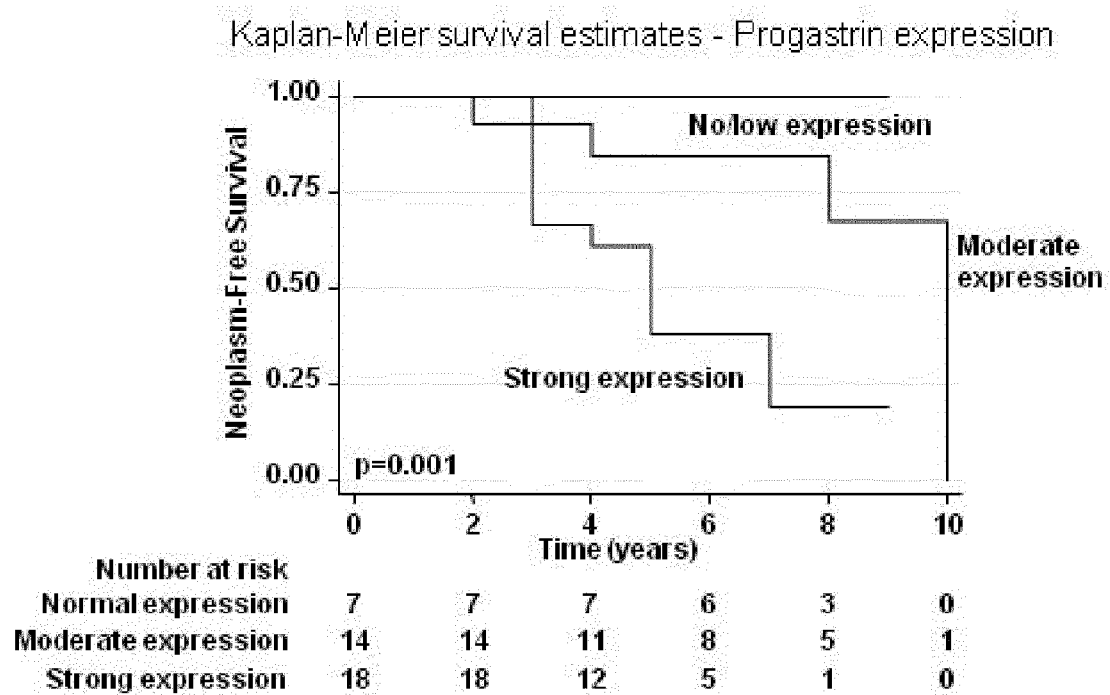

FIG. 4. Kaplan Meier survival curves.

A. Overall neoplasm-free Survival among patients with a coloscopic follow-up, B. Neoplasm-free Survival among patients with a coloscopic follow-up, according to progastrin staining p-value corresponds to logrank univariate analysis.

FIG. 5. Receiver operating characteristic curves.

A: For progastrin staining B: For age. a-Threshold had a 100% sensitivity and the optimal specificity. Se: Sensitivity, Spe: specificity, PG: percentage of progastrin staining, y.o.: years old FIG. 6. Classification tree using variables significantly associated with neoplasm occurrence after multivariate analysis (Progastrin staining and age).

TABLE 1

Clinical and immunohistological features

| Variables | Whole cohort n = 74 % [95% CI] | Patients with coloscopic follow up n = 39 % [95% CI] | p-value |
|---|---|---|---|
| Age (y.o) | | | 0.09 |
| Median | 65 | 64 | |
| Range | 32-89 | 33-89 | |
| Sex | | | 0.68 |
| Male | 57% [45-68] | 59% [42-74] | |
| Female | 43% [32-55] | 41% [26-58] | |
| Number of polyps | | | 0.89 |
| 1 | 59% [47-71] | 62% [45-77] | |
| 2-4 | 41% [29-53] | 38% [23-55] | |
| Size of polyps (largest diameter, mm) | | | 0.49 |
| Median | 3 | 3 | |
| Range | 1-6 | 1-5 | |
| Localisation | | | 0.60 |
| Proximal colon | 20% [12-31] | 18% [8-34] | |
| Distal colon | 80% [69-88] | 82% [66-82] | |
| Occurrence of metachronous adenoma | NA | 41% [26-59] | — |
| loss of expression of MLH1 | 0% [0-5]* | 0% [0-9]* | NC |
| Expression of progastrin | | | 0.26 |
| No/Low expression (<10%) | 26% [16-37] | 18% [8-34] | |
| Moderate expression (10%-50%) | 34% [23-46] | 36% [21-53] | |
| High expression (>50%) | 40% [29-53] | 46% [30-63] | |

Table 1: Progastrin expression was recorded as "No/low moderate or high expression with the percentage of positive colonic epithelial cells. The "physiological" threshold of progastrin expression was determined using the 95th percentile of percentage of stained cells in normal colonic tissue (10% of positive cells).
Chi 2 tests (for categorical variables) and Student tests (for continuous variables) were performed to compare clinical and immune-histological features between patients who had a coloscopic follow up and those who had not.
95% CI: Binomial exact 95-confidence interval was calculated for each percentage.
*One-sided, 97.5% confidence interval.
NA: not available,
NC: not calculable.

TABLE 2

Neoplasm-free survival according to clinical and immunohistological features

| | | Neoplasm-free Survival | | | |
|---|---|---|---|---|---|
| | | Univariate analysis | | Multivariate analysis | |
| Variables | Median (y) | 5 y.S- [95% CI] | p-value | Hazard Ratio (HR) [95% CI] | p-value |
| Age (y.o) | | | <0.0001 | | 0.011 |
| <64 y.o | 10 | 95% [72-99] | | — | |
| ≥64 y.o. | 5 | 26% [7-51] | | 7.4 [1.6-34] | |
| Sex | | | 0.4658 | | |
| Male | NR | 77% [54-90] | | | |
| Female | 10 | 51% [23-73] | | | |
| Number of polyps | | | 0.4064 | | |
| 1 | 10 | 73% [51-87] | | | |
| 2-4 | 7 | 56% [27-78] | | | |
| Size of polyps (largest diameter, mm) | | | 0.0637 | | 0.329 |
| <3 mm | NR | 76% [47-90] | | — | |
| 3-6 mm | 7 | 60% [35-78] | | 1.5 [0.79-2] | |
| Localisation | | | 0.1378 | | 0.799 |
| Proximal colon | 5 | 43% [10-73] | | — | |
| Distal colon | 10 | 74% [54-86] | | 1.1 [0.3-4] | |
| Expression of progastrin | | | 0.001 | | |
| Low/no expression (<10%) | NR | 100% [NC] | | — | |
| Moderate expression (10-50%) | 10 | 84% [50-96] | | NC | |
| High expression (>50%) | 5 | 38% [15-61] | | 1.6e09 [4e09-7e10] | <0.0001 |

Table 2: Neoplasm-free survival among patients with colonic hyperplastic polyps who had a coloscopic follow-up.
Multivariate analysis was performed using a cox model including all variables with a p-value <0.20 in the univariate analysis. Final model was obtained after backward stepwise selection, keeping variables with a p-value <0.05.
Y: year, 5y.S.: 5 years-Survival.
95% CI: 95% confident interval was calculated for all 5 years-Survival values.
NR: Not reached,
NC: not calculable.

EXAMPLE

Material & Methods

Study Design

The inventors conducted a monocentric historical cohort study.

Sample Size, Patients and Data Collection

The required sample size for our study main endpoint, Neoplasm-free survival (NFS), was estimated for the logrank test using the method of Freedman and Schoenfeld, with STATA® v11 software (a statistical software package). Thirty-eight patients were required. To demonstrate an association between progastrin staining and neoplasm occurrence, our sample size was calculated to detect a 4-fold increase in the hazard of the case group (minimum hazard ratio (HR) of 4) with 80% power. Based on our preliminary data, the probability of free-neoplasm surviving to the end of the study was set at 0.65 in the control group and prevalence of strong expression of progastrin at 50%.

We reviewed the medical records of all cases of HP diagnosed in the Pathology department of Rangueil Hospital, from 1 Jan. 2000 through 31 Dec. 2001. We excluded cases with a preceding colorectal adenocarcinoma or adenoma, familial colorectal adenocarcinoma history, hyperplastic polyposis, chronic inflammatory bowel disease, insufficient colon site information or follow-up data. The final study group included 74 patients. We also selected 14 normal colonic tissue specimens from resected non-complicated diverticula, 8 adenomas and 6 colorectal adenocarcinomas. Clinical data and medical follow up were collected for all the patients, colonoscopic data for 39 patients. Approval of an institutional research ethics committee was obtained in accordance with the precepts of the Helsinki Declaration.

Immunohistochemistry

For immunohistochemistry on the formaldehyde-fixed, paraffin embedded tissues, primary antibodies were applied overnight and detection was done using the DakoCytomation ENVISION®+ System-HRP (a two-step visualization system including a HRP-labeled polymer conjugated to a secondary antibody). Anti-progastrin antibody (1137) 29 was kindly provided by Pr Shulkes (Melbourne University) and antibodies against MLH1 and MGMT provided by BD Pharmingen.

Analysis of the whole polyp section was performed at ×20 magnification. Progastrin staining was measured by percentage of stained cells. All specimens were examined in a double blinded fashion by two pathologists. Because the inter-rater agreement was excellent (ICC=0.9), percentages were reported as the average results between the two readers.

Statistical Analysis

Univariate analysis was conducted to compare clinical and immunohistochemistry findings between the different study groups using the $Chi^2$ test or Fisher exact test (when required) for categorical variables and Wilcoxon-Mann-Whitney for quantitative variables. We calculated intra-class correlation in order to determine inter-rater agreement for immunohistochemistry staining For neoplastic-free survival analysis, only patients with colonoscopic follow up data were included (39 patients). We performed Kaplan-Meier curves and log rank test to assess the association of progastrin expression with the occurrence of a new colorectal neoplastic event. The main end point was neoplasm-free survival. The time to event was determined as the time interval between the diagnosis of HP and the occurrence of metachronous colorectal adenomas in the same site (proximal or distal colon) as the first HP. Progastrin expression was recorded as low, moderate or high expression with the percentage of positive epithelial cells. The "normality" threshold of progastrin expression (low expression) was determined using the 95th percentile of percentage of stained cells in normal colonic tissue (<10%). Moderate expression of progastrin was defined as staining in 10% to 50% of polyp epithelial cells and high expression as staining in more than 50% of cells. When a patient had more than one polyp, the polyp with the strongest expression of progastrin was retained for evaluation. The log-rank test was also used to assess significance of clinical characteristics. Quantitative variables were recorded into two-class variables using the median. To demonstrate that progastrin was a prognostic factor independent from other clinical factors, cox proportional-hazards model was performed to test the simultaneous influence on disease free survival of all covariate with a p-value<0.20 in the univariate analysis. After a backward-stepwise selection, only significant variables (p<0.05) were kept in the final cox model.

Receiver operating characteristic analysis was then performed to select optimal "diagnostic" threshold for each significant quantitative variable after multivariate analysis. Using the ROC analysis results, we constructed a predictive test based on a composite score with the significant variables, in order to predict the occurrence of a neoplastic event among patient with HP. Performance of this test was measured by sensitivity (Se), specificity (Spe), positive predictive value (PPV) and negative predictive value (NPV). We also constructed a classification tree using the same variables significantly associated with occurrence of a neoplastic event. To validate the classification tree, a bootstrap validation 30,31 (with 100 bootstrap samples) was performed and the misclassification error rate estimated.

In our study, all tests were two-sided and statistical significance was set at a P value of 0.05. Analyses were performed using STATA® v11 (a statistical software package) 32 and R (with "tree" and "ipred").

Results

Patient and Polyps Characteristics

Clinical and pathologic features of patients and their polyps are shown in table 1. For the whole cohort, the median age of patients was 65 year old (y.o.) (sd: 14 y.o) and 43% of the patients were female. All polyps measured less than 1 cm with an average diameter of 3 mm, and the number of polyps at diagnosis was less than 5 for all the patients. Twenty % of HP were localized in the proximal colon and 80% in the distal colon, which is consistent with previous observations. In our sample, none HP displayed the major histological features described for sessile serrated adenomas (SSA), including architectural abnormalities and loss of expression of MLH1 4,10,33 The subset of patients with colonoscopic follow up was representative of the whole cohort since no statistical difference on clinical and immuno-histochemical features was found between patients with a colonoscopic follow up and the ones with a medical follow up. During the follow-up, an occurrence of adenomas at the same colonic location as the initial HP (proximal or distal colon) was found in 41% of the patients. The pathologic type of these metachronous adenomas was tubular adenomas except in one case where a tubulovillous adenoma was observed. Mainly low grade adenomas (38%) were diagnosed and 3% were high grade adenomas.

Progastrin Expression in Normal Colon, Colonic Hyperplastic Polyps, Adenomas and Adenocarcinomas Representative pictures of progastrin staining in the different colon tissues are shown in FIGS. 1 and 2. The percentages of progastrin-positive cells in normal colon, HP, adenomas, and adenocarcinomas are reported in FIG. 3. Progastrin expression in HP was significantly different from the expression in normal colon (respectively, median: 45%, range: 0%-100%; versus 1%, range: 0%-10%, p=0.002). 100% of the tested adenomas or adenocarcinomas displayed an important expression of progastrin. As previously described 26,28, progastrin expression was higher in adenomas and adenocarcinomas than in normal colon (low grade dysplasia adenomas, p=0.001; high grade dysplasia adenomas, p=0.007; adenocarcinomas, p=0.0005).

In normal colon, average percentage of progastrin staining was 2.6% (sd: 3.7%, range: 0-10). We considered, that progastrin staining was low when the percentage of staining was less than the 95th percentile of the normal tissue (<10%). In the whole cohort, weak expression of progastrin (<10%) was found in 26% of the HP. Expression of the prohormone was moderate (10%-50% of staining) in 34% of the HP and high (>50% of staining) in 40% of them (Table 1). The results were not significantly different in the patients group with colonoscopic follow up (weak expression 18%, moderate expression 36%, high expression 46%, p=0.26).

Patient Neoplasm-Free Survival

Survival analysis was performed using data from patients who had at least one colonoscopy during their follow up. As mentioned above, clinical and immunohistological characteristics of these patients did not significantly differ from the other patients of the cohort. The mean duration of follow up was 6 years. Only occurrence of metachronous adenomas at the same site of the HP (proximal or distal colon) was considered as a recurrence event. The overall median of neoplasm-free survival (S50%) was 8 years and survival at 5 years was 67% (95% CI: 49%-80%) (FIG. 4A). Univariate analysis (Table 2) showed a significant association between progastrin overexpression and shortened neoplasm-free survival (p=0.001). Patients with high expression of progastrin had a median neoplasm-free survival of 5 years, whereas during the 10 years following period, the median survival was not reached by patients with low expression of progastrin, since no recurrence occurred (Table 2, FIG. 4B). The 5 years-neoplasm-free survival (5 y.S) for the patients with weak progastrin expression was 100%, this value decreases to 84% for the patients with moderate expression and to 38% for the patients with high expression. In the same way, age was significantly associated with occurrence of adenoma (p<0.0001, for patients who were less than 64 years old: 5 y.S=95% and S50%=10 years vs 5 y.S=26% and S50%=5 years for older patients, Table 2).

To demonstrate that the association between progastrin staining and neoplasm-free survival was independent from the subject's age, HP localisation and HP size, we performed a multivariate analysis (table 2). After adjustment, progastrin expression was still highly significantly associated with adenoma occurrences (p<0.0001). Taken together, these results show that progastrin staining in HP is an independent prognostic factor.

A Predictive Test for Recurrence

Figure 6:
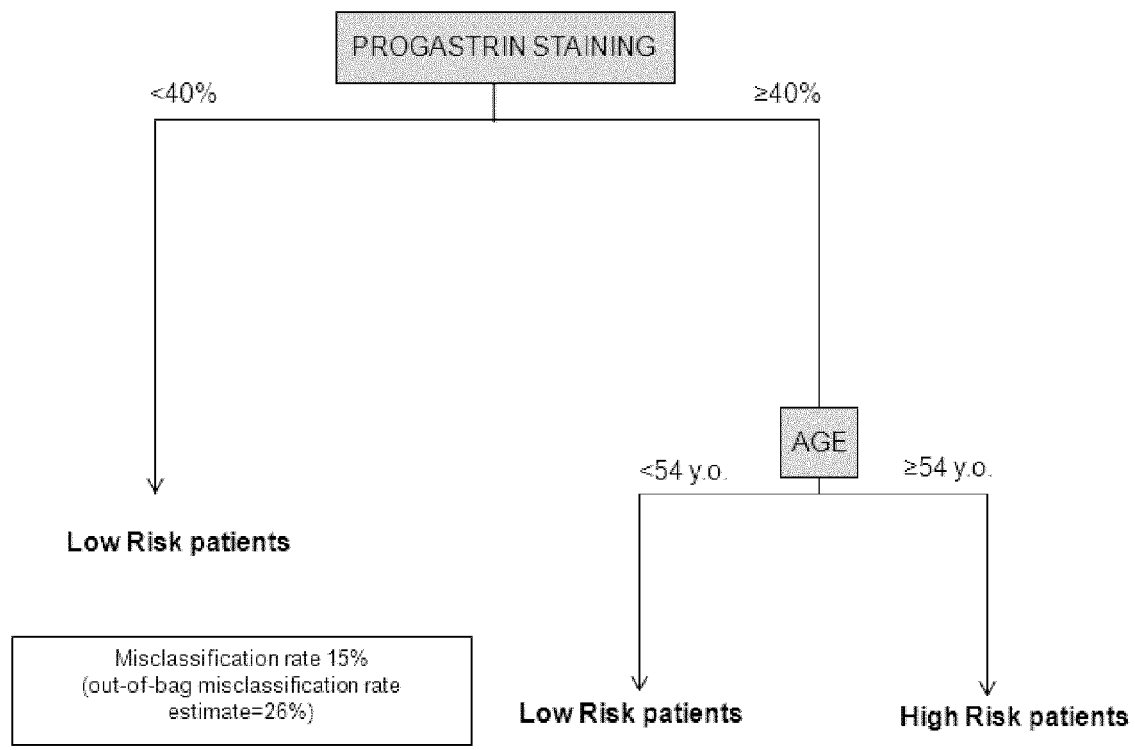

To assess whether a predictive test using progastrin and age can predict occurrence of neoplasm after developing a first HP, we performed the receiver operating characteristic curves for the percentage of progastrin positive cells and for age (FIG. 5). The predictive performance of progastrin and age were estimated by the area under the curve (AUC), which were, respectively, 0.81 (95% CI: 0.68-0.94) and 0.86 (95% CI: 0.74-0.98). Using the ROC curves, we also determined the best "diagnostic" threshold (i.e. with a 100% sensitivity to detect all the patients at risk to develop an adenoma and an optimal specificity) for each parameter in order to construct a classification tree. For progastrin staining, we chose the 40%—threshold (Sensitivity (Se)=100% and specificity (Spe)=57%) and for age the 54 y.o-threshold (Se=100% and Spe=48%). The classification tree, calculated with R software, shows that all patients with less than 40% of progastrin positive HP cells can be considered "at low risk". Among patients with more than 40% of PG staining in HP, only patients older than 54 y.o. can be considered as "at high risk" (FIG. 6). This composite test had a sensitivity of 100% (95% CI: 79%-100%), a specificity of 74% (51%-90%), a positive predictive value of 73% 95% CI: 50%-89%) and a negative predictive value of 100% (95% CI: 81%-100%). Misclassification error rate was 15% in our study sample. To estimate generalization error of classification, a bootstrap validation was performed. The out-of-bag misclassification error estimate was 25.6%. Among misclassification errors, no false negative was found and all neoplasm occurrences were detected. Therefore, we established a predictive test based on progastrin staining and patient's age that predicts occurrence of colonic neoplasm after developing a first HP.

Thus, the present invention validates a new biomarker (progastrin) that predicts the occurrence of colonic neoplasm (adenomas, adenocarcinomas) after resection of HP. This prognostic tool identifies with a very high sensitivity (100%) the subset of patients at high risk for developing a colonic neoplasm who could benefit from a more suitable follow up strategy.

REFERENCES

Throughout this application, various references describe the state of the art to which this invention pertains. The disclosures of these references are hereby incorporated by reference into the present disclosure.

Baldwin G S, Hollande F, Yang Z, et al: Biologically active recombinant human progastrin (6-80) contains a tightly bound calcium ion. J Biol Chem 276:7791-6, 2001.

Bond J H: Polyp guideline: diagnosis, treatment, and surveillance for patients with colorectal polyps. Practice Parameters Committee of the American College of Gastroenterology. Am J Gastroenterol 95:3053-63, 2000.

Brown D, Yallampalli U, Owlia A, et al: pp 60c-Src Kinase mediates growth effects of the full-length precursor progastrin)-80 peptide on rat intestinal epithelial cells, in vitro. Endocrinology 144:201-11, 2003.

Ferrand A, Bertrand C, Portolan G, et al: Signaling pathways associated with colonic mucosa hyperproliferation in mice overexpressing gastrin precursors. Cancer Res 65:2770-7, 2005.

Ferrand A, Wang T C: Gastrin and cancer: a review. Cancer Lett 238:15-29, 2006.

Goldstein N S, Bhanot P, Odish E, et al: Hyperplastic-like colon polyps that preceded microsatellite-unstable adenocarcinomas. Am J Clin Pathol 119:778-96, 2003.

Grabowska A M, Hughes J, Watson S A: Use of interfering RNA to investigate the role of endogenous gastrin in the survival of gastrointestinal cancer cells. Br J Cancer 96:464-73, 2007.

Huang E H, Whelan R L, Gleason N R, et al: Increased incidence of colorectal adenomas in follow-up evaluation of patients with newly diagnosed hyperplastic polyps. Surg Endosc 15:646-8, 2001.

Hollande F, Lee D J, Choquet A, et al: Adherens junctions and tight junctions are regulated via different pathways by progastrin in epithelial cells. J Cell Sci 116:1187-97, 2003.

Jass J R: Hyperplastic polyps and colorectal cancer: is there a link? Clin Gastroenterol Hepatol 2:1-8, 2004.

Jass J R, Young J, Leggett B A: Hyperplastic polyps and DNA microsatellite unstable cancers of the colorectum. Histopathology 37:295-301, 2000.

Nemeth J, Taylor B, Pauwels S, et al: Identification of progastrin derived peptides in colorectal carcinoma extracts. Gut 34:90-5, 1993.

Renaut A J, Douglas P R, Newstead G L: Hyperplastic polyposis of the colon and rectum. Colorectal Dis 4:213-215, 2002.

Rex D K, Johnson D A, Anderson J C, et al: American College of Gastroenterology guidelines for colorectal cancer screening 2009 [corrected]. Am J Gastroenterol 104:739-50, 2009.

Siddheshwar R K, Gray J C, Kelly S B: Plasma levels of progastrin but not amidated gastrin or glycine extended gastrin are elevated in patients with colorectal carcinoma. Gut 48:47-52, 2001.

Singh P, Velasco M, Given R, et al: Progastrin expression predisposes mice to colon carcinomas and adenomas in response to a chemical carcinogen. Gastroenterology 119:162-71, 2000.

Singh P, Lu X, Cobb S, et al: Progastrin1-80 stimulates growth of intestinal epithelial cells in vitro via high-affinity binding sites. Am J Physiol Gastrointest Liver Physiol 284:G328-39, 2003.

Torlakovic E, Skovlund E, Snover D C, et al: Morphologic reappraisal of serrated colorectal polyps. Am J Surg Pathol 27:65-81, 2003.

Umar S, Sarkar S, Cowey S, et al: Activation of NF-kappaB is required for mediating proliferative and antiapoptotic effects of progastrin on proximal colonic crypts of mice, in vivo. Oncogene 27:5599-611, 2008.

Van Solinge W W, Nielsen F C, Friis-Hansen L, et al: Expression but incomplete maturation of progastrin in colorectal carcinomas. Gastroenterology 104:1099-107, 1993.

Wang T C, Koh T J, Varro A, et al: Processing and proliferative effects of human progastrin in transgenic mice. J Clin Invest 98:1918-29, 1996.

Wu H, Owlia A, Singh P: Precursor peptide progastrin (1-80) reduces apoptosis of intestinal epithelial cells and upregulates cytochrome c oxidase Vb levels and synthesis of ATP. Am J Physiol Gastrointest Liver Physiol 285:G1097-110, 2003.

The invention claimed is:

1. A method for treating a patient at least 54 years of age after resection of hyperplastic polyps, said method comprising the steps of contacting a tissue sample of a hyperplastic polyp from said patient with a binding partner capable of selectively interacting with progastrin, detecting binding partner that is bound to progastrin in said sample in order to quantify a percentage of epithelial cells in said sample that express progastrin, determining that said patient is at high risk of developing a colonic neoplasia if more than 40% of the epithelial cells in the sample express progastrin, and administering to said patient determined to be at high risk of developing colonic neoplasia an antibody specific for progastrin.

2. The method according to claim 1, wherein the level of progastrin expression is determined by immunohistochemistry.

3. The method according to claim 1, wherein the colonic neoplasia is a colorectal cancer.

4. The method according to claim 1, wherein the colonic neoplasia is a colorectal adenocarcinoma or colorectal adenoma.

\* \* \* \* \*

---

SEQUENCE LISTING

```
<160> NUMBER OF SEQ ID NOS: 1

<210> SEQ ID NO 1
<211> LENGTH: 80
<212> TYPE: PRT
<213> ORGANISM: Homo sapiens

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80
```